United States Patent [19]

Katayama et al.

[11] Patent Number: 5,180,420
[45] Date of Patent: Jan. 19, 1993

[54] WATER DISPERSIBLE GRANULES

[75] Inventors: Yasuyuki Katayama, Takarazuka; Yasuhiko Ishimoto, Nishinomiya; Fumio Horide, Ikeda; Shigenori Tsuda, Kyoto; Fumio Nishioka, Toyonaka, all of Japan

[73] Assignee: Sumitomo Chemical Company, Limited, Osaka, Japan

[21] Appl. No.: 667,759

[22] Filed: Mar. 11, 1991

[30] Foreign Application Priority Data

Mar. 15, 1990 [JP] Japan .................. 2-065774

[51] Int. Cl.$^5$ .......................... A01N 43/653
[52] U.S. Cl. ............... 504/116; 71/DIG. 1; 514/230.5; 514/383; 514/394; 514/395; 514/417; 514/421; 514/476; 514/478; 514/486; 514/487; 514/488; 514/489; 514/490; 514/770; 514/951; 514/952
[58] Field of Search ............... 71/92, DIG. 1, 95, 106, 71/107, 108, 111, 904; 514/230.5, 383, 394, 395, 417, 421, 476, 478, 486, 487, 488, 489, 490, 770, 951, 952

[56] References Cited

U.S. PATENT DOCUMENTS 3,920,442 11/1975 Albert et al. .................. 71/93
3,954,439 5/1976 Papamichael et al. ........... 71/88
4,554,007 11/1985 Funaki et al. ................. 71/92

FOREIGN PATENT DOCUMENTS 57-163303 10/1982 Japan .
59-193803 11/1984 Japan .

OTHER PUBLICATIONS

Farm Chemicals Handbook '87, Willoughby (Ohio), Meister Publishing Co., 1987, pp. C131 and C146.
McCutcheon's Detergents & Emulsifiers, Ridgewood (New Jersey), Allured Publishing Corp., 1971, p. 23.
Derwent Central Patents Index, Basic Abstracts Journal, week 8508, Apr. 17, 1985, Section C:AGDOC, Class CO3, Abstract No. 046638/08, Derwent Publications Ltd, London, GB; & JP-A-60 004 100 (Showa Denko K.K.) Oct. 1, 1985.

*Primary Examiner*—Allen J. Robinson
*Assistant Examiner*—John D. Pak
*Attorney, Agent, or Firm*—Stevens, Davis, Miller & Mosher

[57] ABSTRACT

The water dispersible granule of the present invention contains (a) a pesticidal active ingredient which is solid at room temperature, (b) an anionic surface active agent, and (c) a kaolin series clay having a volume median diameter of 2 μm or more, and it exhibits a good disintegrability-in-water and a high dispersion stability.

7 Claims, No Drawings

WATER DISPERSIBLE GRANULES

The present invention relates to a water dispersible granule (hereinafter referred to as WDG) of pesticides which has a good disintegrability-in-water and a high dispersion stability.

WDG is a formulation obtained by mixing finely-pulverized active ingredients, surface active agents and if necessary other auxiliaries and granulating the mixture into a granule, and capable of disintegrating into a dispersion of fine particles when being diluted with water.

The present inventors have extensively studied to improve the disintegrability-in-water and dispersibility-in-water of WDG, and as a result, have found that a WDG having a good disintegrability-in-water and a high dispersion stability is obtained by using as a carrier kaolin clay of which the volume median diameter is prescribed as 2 μm or more. The present inventors thus completed the present invention.

According to the present invention, there is provided a pesticidal WDG comprising (a) a pesticidally active ingredient which is solid at room temperature, (b) an anionic surface active agent and (c) a kaolin clay having a volume median diameter of 2 μm or more. The WDG of the present invention easily disintegrates, for example, even in water having a hardness as high as 200 ppm or more, and besides shows a high suspensibility.

The WDG of the present invention will be described below.

Specific examples of the pesticidally active ingredient referred to in the present invention are compounds which are solid at room temperature and useful as pesticides such as insecticides, fungicides, herbicides, plant growth regulators, etc., and a mixture of two or more of them. Of the compounds which are solid at room temperature, those having a melting point of about 70° C. or more are particularly preferred. Referring specifically to the pesticidally active ingredient, the following can be given, but the pesticidally active ingredient of the present invention is not of course limited thereto. Also, as a matter of course, it includes its active geometrical isomers, optical isomers and a mixture thereof.

| Compound No. | Name of compound |
|---|---|
| (1) | (E)-1-(4-Chlorophenyl)-4,4-dimethyl-2-(1,2,4-triazol-1-yl)-1-penten-3-ol |
| (2) | (E)-1-(4-Chlorophenyl)-4,4-dimethyl-2-(1,2,4-triazol-1-yl)-1-penten-(S)-3-ol |
| (3) | (E)-1-(2,4-Dichlorophenyl)-4,4-dimethyl-2-(1,2,4-triazol-1-yl)-1-penten-3-ol |
| (4) | 7-Fluoro-6-[(3,4,5,6-tetrahydro)-phthalimido]-4-(2-propynyl)-1,4-benzoxazin-3(2H)-one |
| (5) | N-[4-Chloro-2-fluoro-5-{(1-methyl-2-propynyl)oxy}phenyl]-3,4,5,6-tetrahydrophthalimide |
| (6) | 1-Methylethyl-(3,4-diethoxyphenyl)carbamate |
| (7) | 3-(3,5-Dichlorophenyl)-1,5-dimethyl-3-azabicyclo[3.1.0]hexane-2,4-dione |
| (8) | Methyl benzimidazol-2-ylcarbamate |

The concentration of these active ingredients in the formulation is not critical. However, it is suitably within the range of 10 to 70% by weight in terms of ease of granulation and biological activity. When the active ingredient has a high activity at low dosage rates, the concentration preferably falls in the range of 10 to 50% by weight.

Specific examples of the anionic surface active agent referred to in the present invention are dispersible high molecular compounds such as naphthalenesulfonate/formaldehyde condensates, alkylnaphthalenesulfonate/formaldehyde condensates, lignosulfonates, polycarboxylic acids, etc. Preferably, however, naphthalenesulfonate/formaldehyde condensates, alkylnaphthalenesulfonate/formaldehyde condensates and lignosulfonates are used.

In the present invention, the content of the anionic surface active agents in the formulation is generally 5 to 25% by weight, preferably 8 to 12% by weight, but it may be properly changed.

The kaolin clay used in the present invention refers mineralogically to clayey minerals containing as a component kaoline mineral defined as a mineral group having the 1:1 stratified structure of a tetrahedral silicate sheet and an octahedral alumina or magnesium-oxide sheet (kaolinite subgroup or serpentine subgroup, respectively). Specifically, there are mentioned clay containing kaoline mineral group as a main component. Even if clay contains other mineral groups not belonging to the kaolin mineral group such as pyrophyllite, talc, smectite, mica clay, etc. which have the 2:1 stratified structure of the tetrahedral sheet and the octahedral sheet, it is included in the kaolin clay of the present invention when it contains kaolin mineral.

In the present invention, the volume median diameter of the kaolin clay is 2 μm or more, generally, 2 to 10 μm inclusive, preferably 2 to 8 μm inclusive. Specifically speaking, there are mentioned ASP-400P containing as a main component kaoline mineral of 2 μm to 10 μm in volume median diameter (produced by Engelhard Corp.), SP Clay (produced by Shokozan), Fubasami M Clay, Fubasami MS Clay and Fubasami MF Clay (produced by Fubasami Clay Co., Ltd.), comprising two components of a kaoline mineral and pyrophyllite. The kaolin clay of the present invention, however, is not limited thereto.

In the present invention, the content of the kaolin series clay in the formulation is usually 10 to 80% by weight, but it may be changed depending upon the contents of the active ingredient and surface active agent in the formulation. The content is preferably 35% by weight or more in terms of ease of granulation, and more preferably 50% by weight or more in terms of improvement of the disintegrability-in-water of WDG.

In order to impart wettability to the WDG of the present invention, naphthalenesulfonates, alkylnaphthalenesulfonates, alkylbenzenesulfonates, alkyl sulfates, alkylallylsulfonates, etc. may be incorporated in the WDG as a wetting agent. It is preferable, however, to add anionic surface active agents such as naphthalenesulfonates, alkylnaphthalene-sulfonates, etc. The amount of the anionic surface active agents added is generally 1 to 5% by weight, preferably 2 to 3% by weight.

The WDG of the present invention is produced by the common pan granulation method, extrusion method and high speed mixing method.

The pan granulation method is a method comprising mixing and finely pulverizing active ingredient, dispersing agent, wetting agent, other auxiliaries and mineral carrier such as a kaolin clay and granulating the finely-pulverized mixture on a pan granulator while adding water. The extrusion method is a method comprising granulating the same finely-pulverized mixture as used in the pan granulation method on an extrusion granulator while adding water. These pan granulation method and extrusion method are preferable manufacturing methods among various granulation methods because the granulation equipment and running cost are cheap and WDG produced by granulation has a good dispersibility-in-water.

The WDG is usually applied to fields after dilution with water of several hundred to several thousand times as much. It is a formulation which is easy for users to handle because there is no dusting at the time of dilution unlike wettable powders and volumetric measuring is possible.

The present invention will be illustrated in more detail with reference to the following examples, comparative examples and test examples, but it is not to be interpreted as being limited thereto.

In the examples, the active ingredient is shown by the foregoing Compound No., and parts are by weight.

EXAMPLE 1

Each of the kaolin clays having a volume median diameter of 2 μm or more shown in Table 1 was added to 25 parts of the compound (3), 10 parts of a sodium naphthalenesulfonate/formaldehyde condensate and 1.5 parts of sodium alkylnaphthalenesulfonate so that the total weight was 100 parts. The mixture was thoroughly mixed in a bag and finely pulverized by means of an air mill. The pulverized product was charged to a pan granulator having a diameter of 40 cm and shaped into granules while rotating the granulator at 45 rpm and spraying about 20 parts of distilled water per 100 parts of the powder by means of a hand sprayer. The granulated product was dried in a fluidized dryer at 50° C. for 20 minutes, and sieved to collect a fraction of 14- to 30-mesh size. Thus, a WDG containing 25% of the compound (3) was obtained (hereinafter present formulation (1)).

EXAMPLE 2

ASP-400P (kaolin clay produced by Engelhard Corp.) was added to 25 parts of the compound (3), a varying amount (5, 7.5, 12.5, 15 and 20 parts) of a sodium naphthalenesulfonate/formaldehyde condensate and 1.5 parts of sodium alkylnaphthalenesulfonate so that the total weight was 100 parts. Every mixture was thoroughly mixed in a bag and finely pulverized by means of an air mill. The pulverized product was charged to a pan granulator having a diameter of 40 cm and shaped into granules while rotating the granulator at 45 rpm and spraying about 17 to 27 parts of distilled water per 100 parts of the powder by means of a hand sprayer. Every granulated product was dried in a fluidized dryer at 50° C. for 20 minutes, and sieved to collect a fraction of 14- to 30-mesh size. Thus, a WDG containing 25% of the compound (3) was obtained (hereinafter present formulation (2)).

EXAMPLE 3

SP Clay (kaolin clay produced by Shokozan) was added to 25 parts of the compound (3), 10 parts of sodium lignosulfonate shown in Table 3 and 1.5 parts of sodium alkylnaphthalenesulfonate so that the total weight was 100 parts. The mixture was thoroughly mixed in a bag and finely pulverized by means of an air mill. The pulverized product was charged to a pan granulator having a diameter of 40 cm and shaped into granules while rotating the granulator at 45 rpm and spraying about 17 to 27 parts of distilled water per 100 parts of the powder by means of a hand sprayer. The granulated product was dried in a fluidized dryer at 50° C. for 20 minutes, and sieved to collect a fraction of 14- to 30-mesh size. Thus, a WDG containing 25% of the compound (3) was obtained (hereinafter present formulation (3)).

EXAMPLE 4

Each of the above-described ASP-400P and the above-described SP Clay was added to 10 parts of each of the compounds (2) and (3), 10 parts of a sodium naphthalenesulfonate/formaldehyde condensate and 1.5 parts of sodium alkylnaphthalenesulfonate so that the total weight was 100 parts. Every mixture was thoroughly mixed in a bag and finely pulverized by means of an air mill. The pulverized product was charged to a pan granulator having a diameter of 40 cm and shaped into granules while rotating the granulator at 45 rpm and spraying about 20 parts of distilled water per 100 parts of the powder by means of a hand sprayer. Every granulated product was dried in a fluidized dryer at 50° C. for 20 minutes, and sieved to collect a fraction of 14- to 30-mesh size. Thus, a WDG containing 10% of each of the compounds (2) and (3) was obtained (hereinafter present formulation (4)).

EXAMPLE 5

Fubasami M Clay (kaolin clay produced by Fubasami Clay Co., Ltd.) was added 25 parts of each of the compounds (6), (7) and (8), 10 parts of a sodium naphthalenesulfonate/formaldehyde condensate and 1.5 parts of sodium alkylnaphthalenesulfonate so that the total weight was 100 parts. Every mixture was thoroughly mixed in a bag and finely pulverized by means of an air mill. The pulverized product was charged to a pan granulator having a diameter of 40 cm and shaped into granules while rotating the granulator at 45 rpm and spraying about 18 parts of distilled water per 100 parts of the powder by means of a hand sprayer. Every granulated product was dried in a fluidized dryer at 50° C. for 20 minutes, and sieved to collect a fraction of 14- to 30-mesh size. Thus, a WDG containing 25% of each of the compounds (6), (7) and (8) was obtained (hereinafter present formulation (5)).

EXAMPLE 6

Each of the above-described ASP-400P and the above-described SP-Clay was added to a varying amount (10 and 25 parts) of the compound (4), 10 parts of a sodium naphthalenesulfonate/formaldehyde condensate and 1.5 parts of sodium alkylnaphthalenesulfonate so that the total weight was 100 parts. Every mixture was thoroughly mixed in a bag and finely pulverized by means of an air mill. The pulverized product was charged to a pan granulator having a diameter of 40 cm and shaped into granules while rotating the granulator at 45 rpm and spraying about 18 parts of distilled water per 100 parts of the powder by means of a hand sprayer. Every granulated product was dried in a fluidized dryer at 50° C. for 20 minutes, and sieved to collect a fraction of 14- to 30-mesh size. Thus, a WDG containing 10% of the compound (4) and a WDG containing 25% of the compound (4) were obtained (hereinafter present formulation (6)).

EXAMPLE 7

Each of the above-described ASP-400P and the above-described SP-Clay was added to a varying amount (10 and 25 parts) of the compound (5), 10 parts of a sodium naphthalenesulfonate/formaldehyde condensate and 1.5 parts of sodium alkylnaphthalenesulfonate so that the total weight was 100 parts. Every mixture was thoroughly mixed in a bag and finely pulverized by means of an air mill. The pulverized product was charged to a pan granulator having a diameter of 40 cm and shaped into granules while rotating the granulator at 45 rpm and spraying about 20 parts of distilled water per 100 parts of the powder by means of a hand sprayer. Every granulated product was dried in a fluidized dryer at 50° C. for 20 minutes, and sieved to collect a fraction of 14- to 30-mesh size. Thus, a WDG containing 10% of the compound (5) and a WDG containing 25% of the compound (5) were obtained (hereinafter present formulation (7)).

EXAMPLE 8

Each of the above-described Fubasami M Clay and the above-described ASP-400P was added to 25 parts of each of the compounds (3), (6) and (7), 10 parts of a sodium naphthalenesulfonate/formaldehyde condensate and 1.5 parts of sodium alkylnaphthalenesulfonate so that the total weight was 100 parts. Every mixture was thoroughly mixed in a bag and finely pulverized by means of an air mill. Every pulverized product was put in a mortar and kneaded with 10 to 15 parts of distilled water per 100 parts of the powder. Every kneaded product was extruded through a horizontal-type extrusion-granulator equipped with a screen of 0.8 mm in diameter. The extruded granules were dried in a fluidized dryer at 50° C. for 20 minutes, and sieved to collect a fraction of 10- to 30-mesh size. Thus, a WDG containing 25% of each of the compounds (3), (6) and (7) was obtained (hereinafter present formulation (8)).

COMPARATIVE EXAMPLE 1

A kaolin clay having a volume median diameter of less than 2 μm shown in Table 1 was added to 25 parts of the compound (3), 10 parts of a sodium naphthalenesulfonate/formaldehyde condensate and 1.5 parts of sodium alkylnaphthalenesulfonate so that the total weight was 100 parts. The mixture was thoroughly mixed in a bag and finely pulverized by means of an air mill. The pulverized product was charged to a pan granulator having a diameter of 40 cm and shaped into granules while rotating the granulator at 45 rpm and spraying about 20 parts of distilled water per 100 parts of the powder by means of a hand sprayer. The granulated product was dried in a fluidized dryer at 50° C. for 20 minutes, and sieved to collect a fraction of 14- to 30-mesh size. Thus, a WDG containing 25% of the compound (3) was obtained (hereinafter comparative formulation (1)).

COMPARATIVE EXAMPLE 2

Barden AG-1 (kaolin clay produced by Huber Inc.) was added to 25 parts of the compound (3), a varying amount (5, 7.5, 12.5, 15 and 20 parts) of a sodium naphthalenesulfonate/formaldehyde condensate and 1.5 parts of sodium alkylnaphthalenesulfonate so that the total weight was 100 parts. Every mixture was thoroughly mixed in a bag and finely pulverized by means of an air mill. The pulverized product was charged to a pan granulator having a diameter of 40 cm and shaped into granules while rotating the granulator at 45 rpm and spraying about 17 to 27 parts of distilled water per 100 parts of the powder by means of a hand sprayer. Every granulated product was dried in a fluidized dryer at 50° C. for 20 minutes, and sieved to collect a fraction of 14- to 30-mesh size. Thus, a WDG containing 25% of the compound (3) was obtained (hereinafter comparative formulation (2)).

COMPARATIVE EXAMPLE 3

The above-described Barden AG-1 was added to 25 parts of the compound (3), 10 parts of sodium lignosulfonate shown in Table 3 and 1.5 parts of sodium alkylnaphthalene-sulfonate so that the total weight was 100 parts. The mixture was thoroughly mixed in a bag and finely pulverized by means of an air mill. The pulverized product was charged to a pan granulator of 40 cm in diameter and shaped into granules while rotating the granulator at 45 rpm and spraying about 17 to 27 parts of distilled water per 100 parts of the powder by means of a hand sprayer. The granulated product was dried in a fluidized dryer at 50° C. for 20 minutes, and sieved to collect a fraction of 14- to 30-mesh size. Thus, a WDG containing 25% of the compound (3) was obtained (hereinafter comparative formulation (3)).

COMPARATIVE EXAMPLE 4

Each of the above-described Barden AG-1, ASP-170, ASP-200 and ASP-600 (kaolin clay produced by Engelhard Corp.) was added to 10 parts of each of the compounds (2) and (3), 10 parts of a sodium naphthalenesulfonate/formaldehyde condensate and 1.5 parts of sodium alkylnaphthalenesulfonate so that the total weight was 100 parts. Every mixture was thoroughly mixed in a bag and finely pulverized by means of an air mill. The pulverized product was charged to a pan granulator having a diameter of 40 cm and shaped into granules while rotating the granulator at 45 rpm and spraying about 18 parts of distilled water per 100 parts of the powder by means of a hand sprayer. Every granulated product was dried in a fluidized dryer at 50° C. for 20 minutes, and sieved to collect a fraction of 14- to 30-mesh size. Thus, a WDG containing 10% of each of the compounds (2) and (3) was obtained (hereinafter comparative formulation (4)).

COMPARATIVE EXAMPLE 5

ASP-170 (kaolin clay produced by Engelhard Corp.) was added to 25 parts of each of the compounds (6), (7) and (8), 10 parts of a sodium naphthalenesulfonate/formaldehyde condensate and 1.5 parts of sodium alkylnaphthalenesulfonate so that the total weight was 100 parts. Every mixture was thoroughly mixed in a bag and finely pulverized by means of an air mill. The pulverized product was charged to a pan granulator having a diameter of 40 cm and shaped into granules while rotating the granulator at 45 rpm and spraying about 20 parts of distilled water per 100 parts of the powder by means of a hand sprayer. Every granulated product was dried in a fluidized dryer at 50° C. for 20 minutes, and sieved to collect a fraction of 14- to 30-mesh size. Thus, a WDG containing 25% of each of the compounds (6), (7) and (8) was obtained (hereinafter comparative formulation (5)).

COMPARATIVE EXAMPLE 6

The above-described Barden AG-1 was added to a varying amount (10 and 25 parts) of the compound (4), 10 parts of a sodium naphthalenesulfonate/formaldehyde condensate and 1.5 parts of sodium alkylnaphthalenesulfonate so that the total weight was 100 parts. Every mixture was thoroughly mixed in a bag and finely pulverized by means of an air mill. The pulverized product was charged to a pan granulator having a diameter of 40 cm and shaped into granules while rotating the granulator at 45 rpm and spraying about 20 parts of distilled water per 100 parts of the powder by means of a hand sprayer. Every granulated product was dried in a fluidized dryer at 50° C. for 20 minutes, and sieved to collect a fraction of 14- to 30-mesh size. Thus, a WDG containing 10% of the compound (4) and a WDG containing 25% of the compound (4) were obtained (hereinafter comparative formulation (6)).

COMPARATIVE EXAMPLE 7

The above-described Barden AG-1 was added to a varying amount (10 and 25 parts) of the compound (5), 10 parts of a sodium naphthalenesulfonate/formaldehyde condensate and 1.5 parts of sodium alkylnaphthalene-sulfonate so that the total weight was 100 parts. Every mixture was thoroughly mixed in a bag and finely pulverized by means of an air mill. The pulverized product was charged to a pan granulator having a diameter of 40 cm and shaped into granules while rotating the granulator at 45 rpm and spraying about 20 parts of distilled water per 100 parts of the powder by means of a hand sprayer. Every granulated product was dried in a fluidized dryer at 50° C. for 20 minutes, and sieved to collect a fraction of 14- to 30-mesh size. Thus, a WDG containing 10% of the compound (5) and a WDG containing 25% of the compound (5) were obtained (hereinafter comparative formulation (7)).

COMPARATIVE EXAMPLE 8

Each of the above-described Barden AG-1 and the above-described ASP-170 was added to 25 parts of each of the compounds (3), (6) and (7), 10 parts of a sodium naphthalenesulfonate/formaldehyde condensate and 1.5 parts of sodium alkylnaphthalenesulfonate so that the total weight was 100 parts. Every mixture was thoroughly mixed in a bag and finely pulverized by means of an air mill. Every pulverized product was put in a mortar and kneaded with 10 to 15 parts of distilled water per 100 parts of the powder. Every kneaded product was extruded through a horizontal-type extrusion-granulator equipped with a screen of 0.8 mm in diameter. The granules were dried in a fluidized dryer at 50° C. for 20 minutes. Thus, a WDG containing 25% of each of the compounds (3), (6) and (7) was obtained (hereinafter comparative formulation (8)).

TEST EXAMPLE 1

The suspensibility of the WDG obtained in Example 1 and Comparative Example 1 was determined as follows with diluting the WDG 500 fold with water of 500 ppm hardness at a water temperature of 30° C. After the WDG was put in a cylinder, diluted with water to obtain a suspension and allowed the suspension to stand for 30 minutes. One-tenth the total volume of the suspension was sampled at the central portion of the cylinder and water was removed by means of a rotary evaporator. The active ingredient was extracted and recovered from the residue and quantitatively determined by gas chromatography or liquid chromatography.

The results are shown in Table 1.

TABLE 1

| | Carrier | Volume median diameter of carrier (μm) | Suspensibility (%) |
| --- | --- | --- | --- |
| Present formulation (1) | Fubasami MS Clay | 8.1 | 94 |
| | SP-Clay | 6.7 | 90 |
| | ASP-400P | 4.8 | 90 |
| | Fubasami M Clay | 4.0 | 91 |
| | Fubasami MF Clay | 2.2 | 92 |
| Comparative formulation (1) | ASP-600 | 0.6 | 62 |
| | ASP-200 | 0.4 | 49 |
| | ASP-170 | 0.4 | 47 |
| | Barden AG-1 | 0.3 | 36 |

TEST EXAMPLE 2

The suspensibility of the WDG obtained in Example 2 and Comparative Example 2 was determined with diluting the WDG 500 fold with water of 500 ppm hardness at a water temperature of 30° C. The method was the same as in Test Example 1.

The results are shown in Table 2.

TABLE 2

| | Amount of a naphthalenesulfonate/formaldehyde condensate added (%) | Carrier | Volume median diameter of carrier (μm) | Suspensibility (%) |
| --- | --- | --- | --- | --- |
| Present formulation (2) | 5.0 | ASP-400P | 4.8 | 68 |
| | 7.5 | ASP-400P | 4.8 | 80 |
| | 12.5 | ASP-400P | 4.8 | 89 |
| | 15.0 | ASP-400P | 4.8 | 90 |
| | 20.0 | ASP-400P | 4.8 | 91 |
| Comparative formulation (3) | 5.0 | Barden AG-1 | 0.3 | 23 |
| | 7.5 | Barden AG-1 | 0.3 | 29 |
| | 12.5 | Barden AG-1 | 0.3 | 48 |
| | 15.0 | Barden AG-1 | 0.3 | 62 |
| | 20.0 | Barden AG-1 | 0.3 | 78 |

TEST EXAMPLE 3

The suspensibility of the WDG obtained in Example 3 and Comparative Example 3 was determined with diluting the WDG 500 fold with water of 500 ppm hardness at a water temperature of 30° C. The method was the same as in Test Example 1.

The results are shown in Table 3.

The sulfonation degree means the average number of moles of sulfonic acid group per unit structure of lignin.

TABLE 3

| | Dispersing agent | Carrier | Volume median diameter of carrier (μm) | Suspensibility (%) |
| --- | --- | --- | --- | --- |
| Present formulation (3) | Na lignosulfonate (1) | SP-Clay | 6.7 | 91 |
| | Na lignosulfonate (2) | SP-Clay | 6.7 | 90 |
| | Na lignosulfonate (3) | SP-Clay | 6.7 | 88 |
| Comparative formulation | Na lignosulfonate (1) | Barden AG-1 | 0.3 | 45 |
| | Na lignosulfonate (2) | Barden AG-1 | 0.3 | 50 |

TABLE 3-continued

| | Dispersing agent | Carrier | Volume median diameter of carrier (μm) | Suspensibility (%) |
|---|---|---|---|---|
| (3) | Na lignosulfonate (3) | Barden AG-1 | 0.3 | 41 |

Note:
Na lignosulfonate (1): sulfonation degree of 2.1
Na lignosulfonate (2): sulfonation degree of 1.0
Na lignosulfonate (3): sulfonation degree of 0.9

TEST EXAMPLE 4

The suspensibility of the WDG obtained in Example 4 and Comparative Example 4 was determined with diluting the WDG 500 fold with water of 500 ppm hardness at a water temperature of 30° C. The method was the same as in Test Example 1.

The results are shown in Table 4.

TABLE 4

| | Compound | Carrier | Volume median diameter of carrier (μm) | Suspensibility (%) |
|---|---|---|---|---|
| Present formulation (4) | (2) | ASP-400P | 4.8 | 86 |
| | (2) | SP-Clay | 6.7 | 84 |
| | (3) | ASP-400P | 4.8 | 92 |
| | (3) | SP-Clay | 6.7 | 89 |
| Comparative formulation (4) | (2) | Barden AG-1 | 0.3 | 54 |
| | (3) | Barden AG-1 | 0.3 | 30 |
| | (3) | ASP-170 | 0.4 | 41 |
| | (3) | ASP-200 | 0.4 | 27 |
| | (3) | ASP-600 | 0.6 | 29 |

TEST EXAMPLE 5

The suspensibility of the WDG obtained in Example 5 and Comparative Example 5 was determined with diluting the WDG 500 fold with water of 500 ppm hardness at a water temperature of 30° C. The method was the same as in Test Example 1.

The results are shown in Table 5.

TABLE 5

| | Compound | Carrier | Volume median diameter of carrier (μm) | Suspensibility (%) |
|---|---|---|---|---|
| Present formulation (5) | (6) | Fubasami M Clay | 4.0 | 88 |
| | (7) | Fubasami M Clay | 4.0 | 90 |
| | (8) | Fubasami M Clay | 4.0 | 91 |
| Comparative formulation (5) | (6) | ASP-170 | 0.4 | 54 |
| | (7) | ASP-170 | 0.4 | 48 |
| | (8) | ASP-170 | 0.4 | 36 |

TEST EXAMPLE 6

The suspensibility of the WDG obtained in Example 6 and Comparative Example 6 was determined with diluting the WDG 500 fold with water of 500 ppm hardness at a water temperature of 30° C. The method was the same as in Test Example 1.

The results are shown in Table 6.

TABLE 6

| | Compound | Content of compound (%) | Carrier | Volume median diameter of carrier (μm) | Suspensibility (%) |
|---|---|---|---|---|---|
| Present formulation (6) | (4) | 10 | ASP-400P | 4.8 | 95 |
| | (4) | 25 | ASP-400P | 4.8 | 98 |
| | (4) | 10 | SP-Clay | 6.7 | 98 |
| | (4) | 25 | SP-Clay | 6.7 | 99 |
| Comparative formulation (6) | (4) | 10 | Barden AG-1 | 0.3 | 35 |
| | (4) | 25 | Barden AG-1 | 0.3 | 56 |

TEST EXAMPLE 7

The suspensibility of the WDG obtained in Example 7 and Comparative Example 7 was determined with diluting the WDG 500 fold with water of 500 ppm hardness at a water temperature of 30° C. The method was the same as in Test Example 1.

The results are shown in Table 7.

TABLE 7

| | Content of compound (%) | Carrier | Volume median diameter of carrier (μm) | Suspensibility (%) |
|---|---|---|---|---|
| Present formulation (7) | 10 | ASP-400P | 4.8 | 90 |
| | 25 | ASP-400P | 4.8 | 93 |
| | 10 | SP-Clay | 6.7 | 95 |
| | 25 | SP-Clay | 6.7 | 91 |
| Comparative formulation (7) | 10 | Barden AG-1 | 0.3 | 28 |
| | 25 | Barden AG-1 | 0.3 | 34 |

TEST EXAMPLE 8

The suspensibility of the WDG obtained in Example 8 and Comparative Example 8 was determined with diluting the WDG 500 fold with water of 500 ppm hardness at a water temperature of 30° C. The method was the same as in Test Example 1.

The results are shown in Table 8.

TABLE 8

| | Compound | Carrier | Volume median diameter of carrier (μm) | Suspensibility (%) |
|---|---|---|---|---|
| Present formulation (8) | (3) | Fubasami M Clay | 4.0 | 92 |
| | (3) | ASP-400P | 4.8 | 89 |
| | (6) | Fubasami M Clay | 4.0 | 90 |
| | (6) | ASP-400P | 4.8 | 88 |
| | (7) | Fubasami M Clay | 4.0 | 91 |
| | (7) | ASP-400P | 4.8 | 90 |
| Comparative formulation (8) | (3) | Barden AG-1 | 0.3 | 33 |
| | (3) | ASP-170 | 0.4 | 31 |
| | (6) | Barden AG-1 | 0.3 | 28 |
| | (6) | ASP-170 | 0.4 | 30 |
| | (7) | Barden AG-1 | 0.3 | 33 |
| | (7) | ASP-170 | 0.4 | 27 |

What is claimed is:
1. A water dispersible granule comprising:
   (a) 10 to 70% by weight of a pesticidally active ingredient which is solid at room temperature,

(b) 5 to 25% by weight of an anionic surface active agent, and (c) 10 to 80% by weight of a kaolin clay having a volume median diameter of 2 μm or more.

2. A water dispersible granule according to claim 1, wherein the content of the kaolin clay is 50 to 80% by weight.

3. A water dispersible granule according to claim 1, wherein the anionic surface agent is at least one member selected from the group consisting of naphthalenesulfonate/formaldehyde condensates, alkylnaphthalenesulfonate/formaldehyde condensates and lignosulfonates.

4. A water dispersible granule according to claim 1, wherein the anionic surface active agent is a mixture of (A) at least one member selected from the group consisting of naphthalenesulfonate/formaldehyde condensates, alkylnaphthalenesulfonate/formaldehyde condensates and lignosulfonates and (B) at least one member selected from the group consisting of naphthalenesulfonates, alkylnaphthalenesulfonates, alkylbenzenesulfonates, alkyl sulfates and alkylallylsulfonates.

5. A water dispersible granule according to claim 4, wherein the content of the component (B) is 1 to 5% by weight and the content of the anionic surface active agent is 5 to 25% by weight.

6. A water dispersible granule according to claim 1, wherein the content of the pesticidally active ingredient falls within the range of 10 to 50% by weight.

7. A water dispersible granule according to claim 1, wherein the volume median diameter of kaolin clay falls within the range of 2 to 10 μm.

* * * * *